United States Patent [19]

Luk

[11] 4,187,228

[45] Feb. 5, 1980

[54] ANTIBACTERIAL AGENTS 5R, 2S-HYDROXYMETHYL-3Z (2-HYDROXY- OR 2-ALKOXYETHYLIDENE-1-AZA-4-OXABICYCLO[3,2,0]HEPTANONE

[75] Inventor: Kong Luk, Cranleigh, England

[73] Assignee: Beecham Group Limited, England

[21] Appl. No.: 880,949

[22] Filed: Feb. 24, 1978

[30] Foreign Application Priority Data

Mar. 4, 1977 [GB] United Kingdom ................ 9128/77

[51] Int. Cl.² .................... C07D 263/14; A61K 31/42
[52] U.S. Cl. .................................. 260/245.3; 424/772
[58] Field of Search ................................. 260/307 FA

[56] References Cited

U.S. PATENT DOCUMENTS 4,060,530  11/1977  Howarth et al. ............. 260/307 FA Primary Examiner—Mark L. Berch
Attorney, Agent, or Firm—Jacobs & Jacobs

[57] ABSTRACT

Compounds of the formula (II):

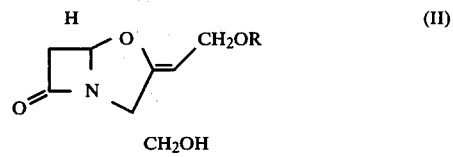

wherein R is hydrogen, is useful for its antibacterial activity and as a synergist for penicillins and cephalosporins.

1 Claim, No Drawings

ANTIBACTERIAL AGENTS 5R, 2S-HYDROXYMETHYL-3Z (2-HYDROXY- OR 2-ALKOXYETHYLIDENE-1-AZA-4-OXABICYCLO[3,2,0]HEPTANONE

This invention relates to a β-lactam containing antibacterial agent, to its preparation and to compositions containing it.

Clavulanic acid, which is of the formula (I):

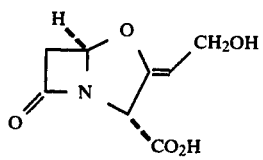

and its esters were disclosed in Belgian Pat. No. 827926 as being potent synergists for penicillins and cephalosporins. It has now been discovered that the carboxyl group of clavulanic acid may be replaced by a hydroxymethyl group without eradicating its useful properties.

Accordingly the present invention provides the compounds of the formula (II):

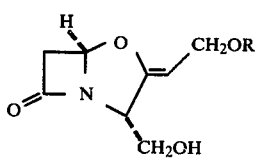

wherein R is a hydrogen atom or a methyl or ethyl group.

Suitably R is a hydrogen atom. Suitably R is a methyl group.

The present invention also provides a process for the preparation of the compounds of the invention which process comprises the reduction of an ester of a compound of the formula (III):

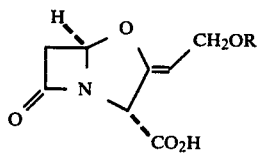

wherein R is a hydrogen atom or a methyl or ethyl group using lithium borohydride.

Most suitably the ester employed is a methyl, ethyl, benzyl, methoxybenzyl or like ester.

A preferred ester for use in the process of the invention is the p-methoxybenzyl ester.

The reduction reaction is carried out in an ether solvent such as tetrahydrofuran under anhydrous conditions. Generally the reaction requires a temperature of about 5°-60° C.

The desired compound may be obtained from the reaction mixture using conventional methods for working-up lithium borohydride reductions.

This invention also provides a pharmaceutical composition which comprises a compound of the formula (II) and a pharmaceutically acceptable carrier therefore.

Most suitably the composition of this invention also comprises a penicillin or cephalosporin.

Suitable forms of the compositions of this invention are as described for esters of clavulanic acid in Belgian Patent No. 827926.

The following Examples illustrate the invention:

EXAMPLE 1

Preparation of 5R, 2S-hydroxymethyl-3Z-(2-hydroxyethylidene)-1-aza-4-oxabicyclo[3,2,0]heptan-7-one.

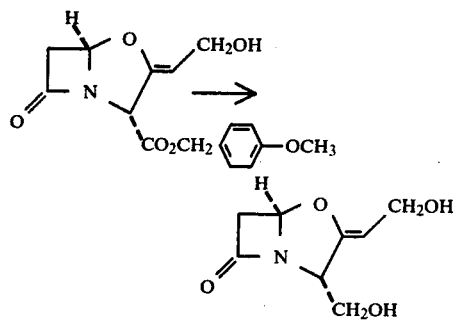

Lithium borohydride (0.3 g, 0.015 mole) was added to a solution of p-methoxybenzyl clavulanate (3.2 g, 0.01 mole) in tetrahydrofuran (50 ml) and the mixture was boiled under reflux for 0.5 h. The cooled reaction mixture was poured into ice-water (50 ml) which was then saturated with sodium chloride. The organic layer was separated and the aqueous layer was extracted with ethyl acetate (2×50 ml). The combined organic extract was dried over magnesium sulphate, filtered, and the filtrate evaporated to give an oil which was chromatographed over silica gel (30 g.). Elution of the column with chloroform-methanol (9:1) afforded 5R-2S-hydroxymethyl-3Z-(2-hydroxyethylidene)-1-aza-4-oxabicyclo[3.2.0] heptan-7-one (0.3 g, 15%), m.p. 93°–97° (from chloroform-carbon tetrachloride), $[\alpha]_D^{20} + 95.0°$ (c, 1.2; H$_2$O), $\nu_{max}$ (CHCl$_3$) 3400 (broad), 1790, 1700, 1310, 1190, 1120, 1040, and 990 cm$^{-1}$, δ(C$_5$D$_5$N) 5.59 (1H, d, J=2.5 Hz, 5-C$\underline{H}$), 4.99 (1H, broad t, J=8 Hz, 8-C$\underline{H}$), 4.79 (1H, broad t, J=4 Hz, 2-C$\underline{H}$), 4.56 (2H, broad d, J=8 Hz, 9-C$\underline{H}_2$), 3.85 (2H, d, J=4 Hz, 10-C$\underline{H}_2$), 3.30 (1H, dd, J=17 Hz, J'=2.5 Hz, 6α-C$\underline{H}$), and 2.85 (1H, d, J=17 hz, 6β-C$\underline{H}$), m/e (relative intensity) 143 (34), 126 (40), 96 (75), 95 (70), and 86 (100) (Found: C, 52.1; H, 6.0; N, 7.25%. C$_8$H$_{11}$NO$_4$ requires C, 51.9; H, 6.0; N, 7.55%).

EXAMPLE 2

Preparation of 5R-2S-Hydroxymethyl-3z-(2-methoxyethylidene)1-aza-4-oxabicyclo[3.2.0]heptan-7-one

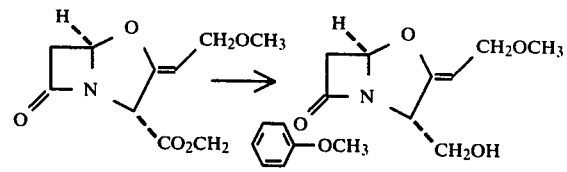

Lithium borohydride (5 mg) was added to a solution of p-methoxybenyl O-methylclavulanate (33 mg) in tetrahydrofuran (5 ml) and the mixture was stirred at room temperature for 0.5 h. The reaction mixture was poured into ice-water (5 ml) which was then saturated with sodium chloride. The organic layer was separated and the aqueous layer was extracted with ethyl acetate (2×5 ml). The combined organic extract was dried over magnesium sulphate, filtered, and the filtrate evaporated to give an oil which was chromatographed over silica gel (5 g). Elution of the column with chloroform-methanol (9:1) afforded the title compound (5 mg), $\nu_{max}$ (liquid film 1790, 1700, 1310, 1190, 1090, 1040, and 755 cm$^{-1}$.

(The starting material for the above reaction may be prepared by the reaction of methoxybenzyl clavulanate with diazomethane in an inert solvent).

I claim:
1. 5R,2S-Hydroxymethyl-3Z-(2-hydroxyethylidene)-1-aza-4-oxa-bicyclo[3.2.0]heptan-7-one.